United States Patent [19]

Sheppard

[11] Patent Number: 5,746,705
[45] Date of Patent: May 5, 1998

[54] ADJUSTABLE ARM SLING AND METHOD OF SUPPORTING AN INJURED ARM

[76] Inventor: John H. Sheppard, 2960 Dacusvile Hwy., Easley, S.C. 29640

[21] Appl. No.: 754,547

[22] Filed: Nov. 21, 1996

[51] Int. Cl.⁶ .................................. A61F 5/00; A61F 5/01
[52] U.S. Cl. .................................. 602/5; 607/4; 607/21
[58] Field of Search .................... 602/4, 5, 12, 20, 602/21, 18, 61–64; 482/10, 17, 91, 67, 131; 128/878, 869, 874; 601/23, 33; 224/265, 201, 908; 248/301, 304

[56] References Cited

U.S. PATENT DOCUMENTS 4,762,256  8/1988  Whitaker ........................ 224/201 X Primary Examiner—Richard J. Apley
Assistant Examiner—Denise Pothier
Attorney, Agent, or Firm—Hardaway Law Firm P.A.

[57] ABSTRACT

An improved arm sling is provided comprising a first elongated member and a second elongated member being joined together, a first curved member extending from the first elongated member and a second curved member extending from the second elongated member, the first curved member for engaging the neck of a user, and the second curved member for supporting an injured arm of the user. The method of using the improved arm sling according to the present invention comprises the steps of connecting the two elongated members, positioning the first curved member around the neck of a user, and supporting an injured arm of the user on the second curved member. The present invention has the advantages of being adjustable in length and being usable on either a right or a left arm.

20 Claims, 3 Drawing Sheets

ADJUSTABLE ARM SLING AND METHOD OF SUPPORTING AN INJURED ARM

BACKGROUND OF THE INVENTION

This invention relates generally to surgical appliances and more particularly to an improved arm sling and method of supporting an injured arm.

Various devices for supporting or resting an arm exist in the prior art. U.S. Pat. No. 2,691,408 to Beard teaches an adjustable arm rest to be used in motor vehicles. More specific to the present invention, U.S. Pat. No. 2,652,050 to Schoeller discloses a surgical arm support comprising a neck band connected to an open hook. U.S. Pat. Nos. 2,807,261 to Strinden and 3,215,138 to Groesbeck disclose arm slings to be positioned around the shoulder of a user.

Despite the prior art devices, there is room for improvement in the art of arm slings.

OBJECTS OF THE INVENTION

It is therefore an object of this invention to provide an improved arm sling.

It is another object of this invention to provide a method of using the improved arm sling according to the present invention to support an injured arm.

It is another object of this invention to provide an improved arm sling that is adjustable in length, thus making it usable by a variety of individuals.

It is yet another object of this invention to provide an improved arm sling that can be used to support either a right or a left arm.

It is yet another object of this invention to provide an improved arm sling that is comfortable to a user.

It is still another object of this invention to provide an improved arm sling that can be put on and adjusted with minimal difficulty.

It is still another object of this invention to provide an improved arm sling that can also be used as a neck exerciser.

These and other objects of the invention are achieved by an adjustable arm sling comprising a first elongated member and a second elongated member; a first curved member, the first curved member extending from the first elongated member; and a second curved member, the second curved member extending from the second elongated member; the first and second elongated members being joined together; the first and second curved members being in different planes.

The method of supporting an injured arm of a user comprises the steps of providing a first elongated member and a second elongated member; providing a first curved member, the first curved member extending from the first elongated member; providing a second curved member, the second curved member extending from the second elongated member; connecting the first and second elongated members; positioning the first curved member on the neck of the user; and supporting the injured arm on the second curved member.

DETAILED DESCRIPTION

According to the present invention, it has been found that an improved arm sling that meets and achieves the various objects of this invention as described above can be utilized. This and other features of the present invention will become apparent from the description that follows with particular reference to the figures of drawing.

Figure 1:
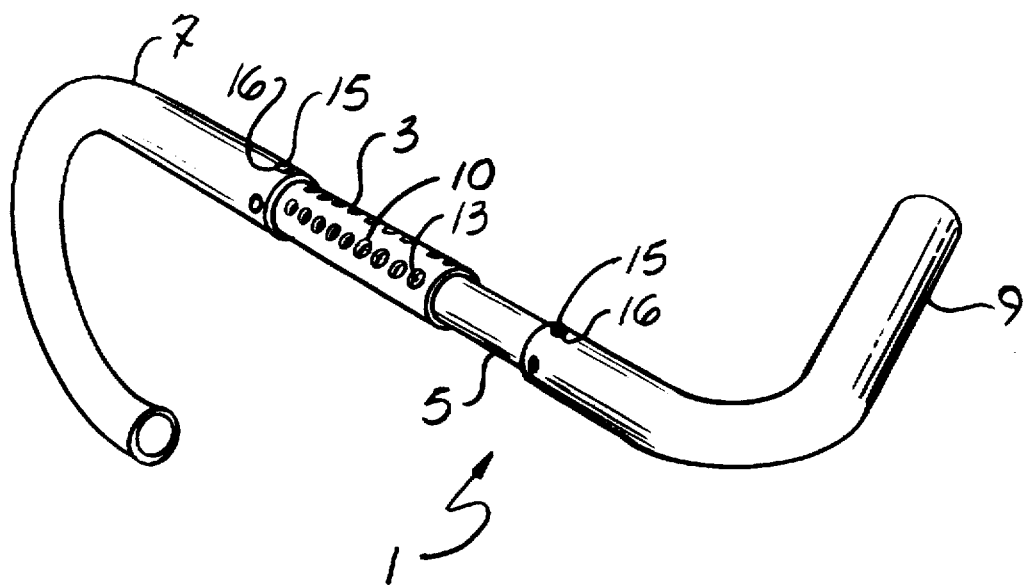
FIG. 1 illustrates a preferred embodiment of an improved arm sling according to the present invention.

Referring to the drawings, FIG. 1 illustrates a preferred embodiment of an adjustable arm sling according to the present invention. Adjustable arm sling 1 comprises a first elongated member 3 and a second elongated member 5. In FIG. 1, a portion of second elongated member 5 is not shown because it is inside of first elongated member 3. Extending from first elongated member 3 is first curved member 7. Extending from second elongated member 5 is second curved member 9. The preferred shape of both elongated members and both curved members is cylindrical.

First curved member 7 and first elongated member 3 are preferably separate pieces joined together. The same is preferred for second curved member 9 and second elongated member 5. First curved member 7 and first elongated member 3, and similarly second curved member 9 and second elongated member 5, may be connected together in a variety of ways. One method of connection involves providing a curved member and an elongated member of different widths with at least one hole in each piece. The hole in the wider piece (16) is shown in FIG. 1. At least a portion of the wider piece should be hollow. In FIG. 1, curved members 7 and 9 are shown to be wider than elongated members 3 and 5, respectively. However, which pieces are to be wider is a design choice. The narrower piece is inserted into the wider piece, and the two are connected by connector 15. Connector 15 can be a conventional threaded connecting item such as a screw (as shown in FIG. 1), or a nut and bolt combination. When connector 15 is a threaded connecting member, it is inserted into and through the hole in each piece. Connector 15 can also be a conventional spring loaded ball bearing inside of the narrower piece which protrudes from the hole in the narrower piece on both sides. While the method of connecting two pieces using a spring loaded ball bearing will be described in further detail later with respect to connecting the two elongated members 3, 5, one skilled in the art could equally use that teaching for joining curved members 7, 9, to elongated members 3, 5, respectively.

Figure 2:
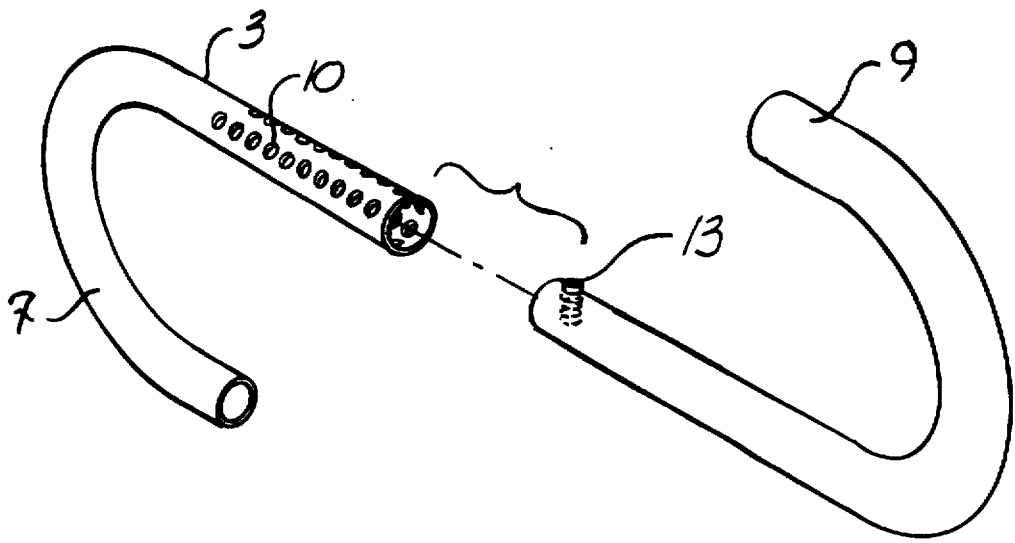
FIG. 2 illustrates an alternative embodiment of an improved arm sling according to the present invention.

Alternatively, first curved member 7 and first elongated member 3 may be secured together with a tight pressure fit or a glued connection, or they may be of unitary construction (as shown in FIG. 2). The same may be true of second curved member 9 and second elongated member 5.

To ready arm sling 1 for use, first elongated member 3 and second elongated member 5 must be connected (i.e., joined) together. In the preferred embodiment, this connection is accomplished as follows. First elongated member 3 and second elongated member 5 are constructed to be generally hollow. Also, first elongated member 3 and second elongated member 5 are of different widths. This design allows for insertion of one of the elongated members into the other. Preferably, the widths are similar enough to where one of the elongated members is inserted into the other with a friction fit for preventing any undesired movement of the elongated members during use of arm sling 1. In FIG. 1, first elongated member 3 is depicted to be wider than second elongated member 5, and thus second elongated member 5 is inserted into first elongated member 3. However, which elongated member is to be wider is a design choice. The wider elongated member, in this case first elongated member 3, defines a plurality of holes 10 therein. Holes 10 are provided at evenly spaced intervals throughout the majority of the length and circumference of first elongated member 3. The narrower elongated member, in this case second elongated member 5, defines at least one hole therein, preferably near an end of secondary elongated member 5 opposite second curved member 9.

A main advantage of the arm sling according to this invention is that its length is adjustable. Therefore, arm sling 1 may be used by a wide variety of people from small children to large athletes. To obtain the desired length of arm sling 1, second elongated member 5 is inserted into first elongated member 3 to the desired depth, making sure that one of holes 10 lines up with the hole in second elongated member 5. Connector 13 is used to join the two elongated members. Connector 13 may be inserted into and through the lined up holes, thereby securing the two elongated members together. Connector 13 is envisioned to be any conventional threaded connecting means, such as a screw (as shown in FIG. 1) or a nut/bolt combination.

Alternatively, as shown in FIG. 2, connector 13 may be a spring loaded ball bearing inside of the hole in second elongated member 5 and protruding from both sides thereof. In this case, the spring loaded ball bearing is compressed when it is inside of first elongated member 3 but not lined up with one of holes 10. Upon lining up with one of holes 10, the ball bearing is released from compression and protrudes from both sides of the hole 10, thereby securing the first and second elongated members together.

While first elongated member 3 and second elongated member 5 are preferably connected as described above, it is within the scope of this invention to connect the two elongated members by any conventional means as long as the length of the arm sling can be easily adjusted.

To change the length of arm sling 1, when connector 13 is a spring loaded ball bearing, the ball bearing is simply compressed from both sides so that it no longer extends out of hole 10. The elongated members are moved relative to one another for lengthening or shortening arm sling 1 as desired, and the ball bearing is released from compression upon lining up with a new hole 10, thereby setting the new length of arm sling 1. When connector 13 is a threaded connecting member, the adjusting process is the same except that the threaded connecting member is removed from both of the elongated members before moving one of them relative to the other, and then reinserted into both upon obtaining the new length of arm sling 1. Similar steps may be used to adjust the angular positioning between first elongated member 3 and second elongated member 5, for reasons discussed below.

Another advantage of the present invention is that arm sling 1 can be substantially worn on either the right or the left side of the body, and, consequently, second curved member 9 can be used to support either the right or the left arm of a user. The adjusting of arm sling 1 for use on another arm is preferably accomplished in either of the following ways. The first way requires that first curved member 7 is connected to first elongated member 3 by connector 15. In this case, first curved member 7 can be rotated around first elongated member 3. This rotation is accomplished by disconnecting first curved member 7 from first elongated member 3, rotating first curved member 7 axially 180 degrees around first elongated member 3, and reconnecting first curved member 7 to first elongated member 3 by connector 15. The second way involves disconnecting the elongated members, axially rotating one of them 180 degrees relative to the other, and reconnecting them. This method would be employed when first curved member 7 is unitary with first elongated member 3, or when a tight pressure fit or a glued connection joins the two members together. Both of these methods essentially rotate first curved member 7 about 180 degrees for wearing arm sling 1 on either side of the body.

Figure 3:
FIG. 3 illustrates a method of using an improved arm sling according to the present invention.

First curved member 7 is preferably U-shaped, whereas the shape of second curved member 9 more closely resembles an 80 degree angle with a curve in place of the vertex. When the two elongated members are joined, first curved member 7 can be positioned on the neck of a user and second curved member 9 can support an injured or lame arm of the user. To accomplish this positioning, first curved member 7 and second curved member 9 are in different, and preferably perpendicular, planes when the two elongated members are joined together. As shown in FIG. 3, when arm sling 1 is worn by a user, first curved member 7 is positioned on the neck of a user and second curved member 9 extends substantially outward, up, and away from the user.

First elongated member 3 and second elongated member 5 are preferably made from steel, whereas first curved member 7 and second curved member 9 are preferably made from plastic. Because the curved members come into contact with the neck and an injured arm of a user, this plastic construction makes arm sling 1 lighter and more comfortable to wear. In the preferred embodiment, both elongated members and both curved members are covered by foam 17, as seen in FIG. 3. Foam 17 is provided to make wearing arm sling 1 as comfortable as possible, in addition to protecting the members from scratches and the like. Foam 17 is preferably made from polyurethane, but may be made from any suitable material.

Having made reference to the structure of the adjustable arm sling according to the present invention, its use will now be described. The method of supporting an injured arm according to the present invention involves using adjustable arm sling 1 in any of its above-described embodiments. Once the two elongated members are connected, first curved member 7 is positioned around the neck of a user. When first curved member 7 and second curved member 9 lie in substantially perpendicular planes, second curved member 9 extends generally outward, up, and away from the body. The injured arm is laid generally perpendicularly across second curved member 9, as shown in FIG. 3.

Figure 4:
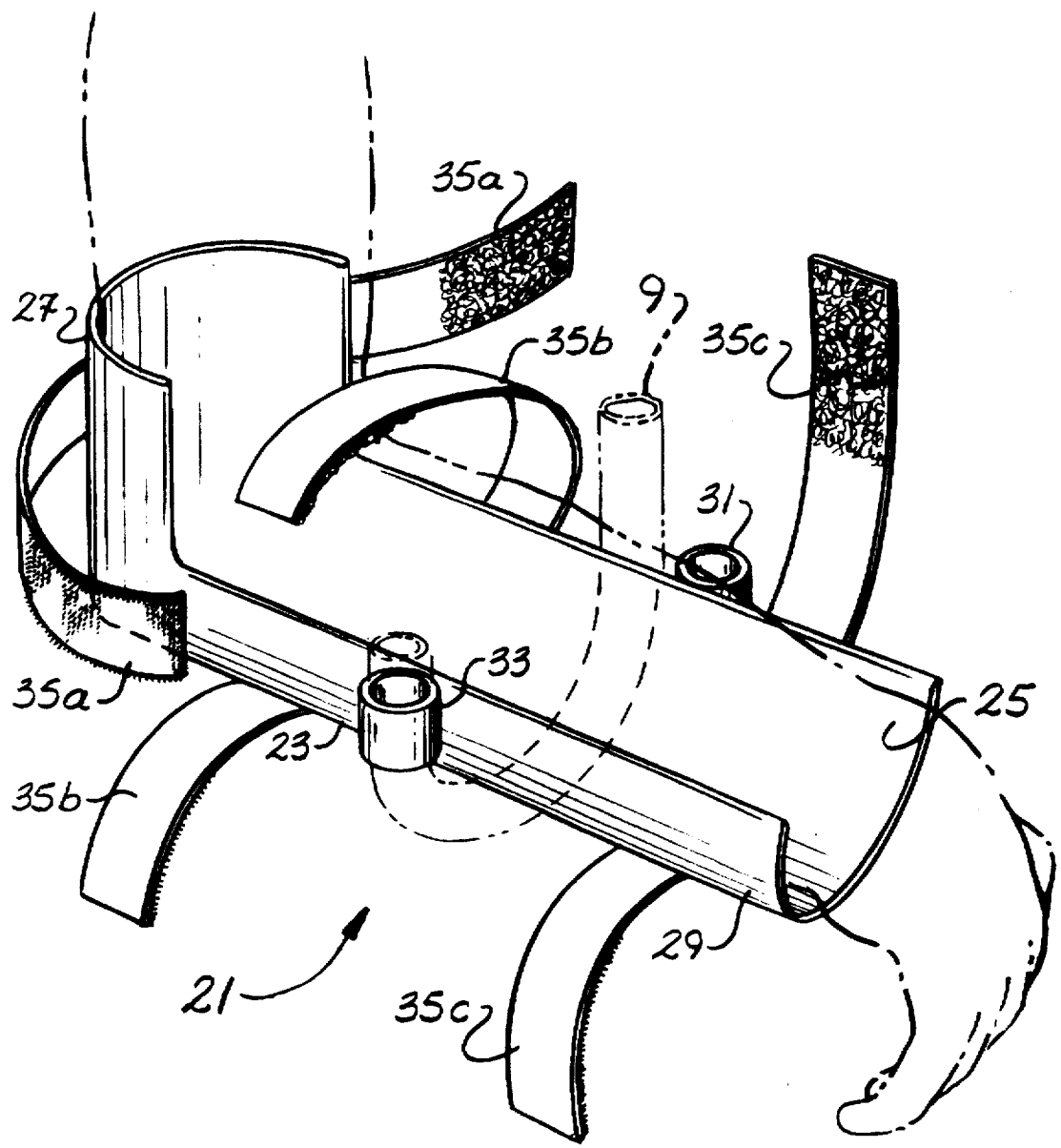
FIG. 4 illustrates an optional arm support for use with the embodiments seen in FIGS. 1 and 2.

As best seen in FIG. 4, an optional arm support 21 may be provided. Support 21 is useful where it is important the entire arm be supported along its length or where limiting the mobility of the elbow, wrist, and\or shoulder is of importance. As seen, support 21 comprises a generally L-shaped semi-tubular structure having an inner arcuate support surface 25 along its entire inner surface. The outer surface defines the complimentary curved shape. An upper bend 27 extends 3–4 inches above horizontal portion 29. Either side of the horizontal portion further defines a means for engaging the preferred arm sling as seen in receptacle or tubes 31 and 33.

As seen, tubes 31 and 33 are not directly opposite one another relative to the support. The offset distance allows a single holder to be used in either a left-handed or right-handed orientation without the inner, unused holder obstructing the sling. Depending upon the desired orientation, the appropriate holder 31 or 33, i.e. the outside holder away from the wearer's body, is selected to engage the terminal free end of curved member 9. In this fashion, the support 21 is cradled by the sling while engaging the respective holder.

Straps 35a–c, preferably having overlapping hook and loop fasteners, may be used to restrain the arm within the support. As a result, the arm and elbow are both supported and protected along their length. Further, additional immobilization of the arm is achieved and may be further enhanced by additional restraints which secure the sling/support assembly to the user's body.

The holder is useful for persons wearing casts or splints, as well as uses where the sling/support is used exclusively. The adjustment features of the sling discussed above are useful in positioning the sling in the most comfortable and effective position to accommodate the optional holder.

While adjustable arm sling 1 is primarily intended to be used for supporting an injured arm, it can also be used as a neck exerciser. A person's neck can be stretched out using the present invention as follows. First curved member 7 is placed on a neck as described above. One hand is used to take hold of a part of arm sling 1 on one side of the neck, and the other hand is used to take hold of arm sling 1 on the other side of the neck. Simultaneously, the person leans his or her head back against upper first curved member 7 and pulls forward with both hands, consequently stretching out the person's neck.

Thus, it is seen that an improved arm sling and a method of using the same can be provided. It is also seen that an improved arm sling that is adjustable in length can be provided. It is also seen that an improved arm sling that can be used to support either a right or a left arm can be provided. It is also seen that an improved arm sling that is comfortable to wear and that can be put on and adjusted with minimal difficulty can be provided. It is also seen that an improved arm sling that can be used as a neck exerciser can be provided.

It is understood that many variations of the present invention will become apparent to one of ordinary skill in the art upon reading the specification. Such variations are within the spirit and scope of the present invention as defined by the following appended claims.

That which is claimed:

1. An adjustable arm sling comprising:
   a first elongated cylindrical member and a second elongated cylindrical member;
   a first curved cylindrical member, said first curved cylindrical member extending from said first elongated cylindrical member;
   a second curved cylindrical member, said second curved cylindrical member extending from said second elongated cylindrical member;
   said first and second elongated cylindrical members being adjustably joined together; and
   said first curved and second curved cylindrical members being axially rotatable relative to each other to occupy different planes,
   wherein said first and second elongated members are generally hollow, said first and second elongated members being of different widths, said wider elongated member defining a plurality of holes therein, said narrower elongated member defining a hole therein, said narrower elongated member being inserted into said wider elongated member, the depth of insertion being determined by the desired length of said arm sling, said elongated members being joined together by a connecting member passing through said hole in said narrower elongated member and one of said plurality of holes of said wider elongated member.

2. The adjustable arm sling according to claim 1 wherein said first and second curved members are in substantially perpendicular planes.

3. The arm sling according to claim 1 wherein said first curved member is connected to said first elongated member, and wherein said second curved member is connected to said second elongated member.

4. The arm sling according to claim 3 wherein said elongated members are made from steel and wherein said curved members are made from plastic.

5. The arm sling according to claim 1 wherein said first curved member and said first elongated member are of unitary construction, and wherein said second curved member and said second elongated member are of unitary construction.

6. The arm sling according to claim 1 wherein said second curved member includes a detachable L shaped support, said support having a sufficient length, width and curvature to support an arm.

7. The arm sling according to claim 6 wherein said detachable L shaped support further defines a means for engaging a terminus of the second curved member, with a holder wherein said holder fits onto said terminus in order to secure said detachable support on said second curved member.

8. The arm sling according to claim 1 wherein said first curved member is U-shaped and wherein the shape of said second curved member is approximately an 80 degree angle with a curved vertex.

9. The arm sling according to claim 1 wherein said connecting member is a threaded connecting member.

10. The arm sling according to claim 1 wherein said connecting member is a spring loaded ball bearing.

11. An adjustable arm sling comprising:
    a first elongated cylindrical member and a second elongated cylindrical member;
    a first curved cylindrical member for engaging the neck of a user, said first curved cylindrical member extending from said first elongated cylindrical member; and
    a second curved cylindrical member for supporting an injured arm of the user, said second curved cylindrical member extending from said second elongated cylindrical member;
    said first and second elongated cylindrical members being adjustably connected together,
    wherein said first curved cylindrical member is connected to said first elongated cylindrical member, further comprising a connecting end of said first elongated cylindrical member containing a plurality of holes, said connecting end communicating with a second elongated cylindrical member having an inserting end with one hole in said second elongated cylindrical member, said one hole containing a connector which communicates with one of said plurality of holes in said connecting end of said first elongated cylindrical member.

12. The arm sling according to claim 11 wherein a first curved cylindrical member can be rotated axially around said first elongated cylindrical member approximately 180 degrees by moving said connector from one of said plurality of holes in said connecting end of said first elongated cylindrical member to another of said plurality of holes, thereby allowing a second curved cylindrical member to support either a right or a left arm of said user.

13. The arm sling according to claim 11 wherein said first elongated cylindrical member can be rotated axially 180 degrees relative to said second elongated cylindrical member partially inserted into said first member, thereby allowing said arm sling to support either a right or a left arm of the user.

14. A method of supporting an injured arm of a user comprising the steps of:

providing a first elongated member and a second elongated member;

providing a first curved member, said first curved member extending from said first elongated member;

providing a second curved member, said second curved member extending from said second elongated member;

connecting said first and second elongated members;

positioning said first curved member on the neck of said user; and supporting said injured arm on said second curved member.

15. The method according to claim 14 further comprising the steps of connecting said first curved member to said first elongated member and connecting said second curved member to said second elongated member.

16. The method according to claim 15 further comprising the steps of disconnecting said first curved member from said first elongated member, rotating said first curved member axially around said first elongated member approximately 180 degrees, and reconnecting said first curved member to said first elongated member, thereby allowing said arm sling to support either a right or a left arm of said user.

17. The method according to claim 14 further comprising the steps of disconnecting one of said elongated members, rotating one said elongated member axially approximately 180 degrees relative to the other said elongated member, and reconnecting said elongated members, thereby allowing said arm sling to support either a right or a left arm of said user.

18. The method according to claim 14 wherein said step of providing a first elongated member and a second elongated member further comprises providing a generally hollow first elongated member and a generally hollow second elongated member, said first and second elongated members being of different widths, said wider elongated member defining a plurality of holes therein, said narrower elongated member defining a hole therein, further comprising the step of inserting said narrower elongated member into said wider elongated member, the depth of insertion being determined by the desired length of said arm sling, and wherein said step of connecting said first and second elongated members further comprises connecting said first and second elongated members by inserting a threaded connecting member into one said hole in each of said elongated members.

19. The method according to claim 14 wherein said step of providing a first elongated member and a second elongated member further comprises providing a generally hollow first elongated member and a generally hollow second elongated member, said first and second elongated members being of different widths, said wider elongated member defining a plurality of holes therein, said narrower elongated member defining a hole therein, further comprising the step of inserting said narrower elongated member into said wider elongated member, the depth of insertion being determined by the desired length of said arm sling, and wherein said step of connecting said first and second elongated members further comprises connecting said first and second elongated members with a spring loaded ball bearing.

20. The arm sling according to claim 19, wherein said plurality of holes on said wider elongated member further comprises a first pattern of linear holes and a second pattern of linear holes.

* * * * *